United States Patent [19]

Tanabe et al.

[11] Patent Number: 5,350,859
[45] Date of Patent: Sep. 27, 1994

[54] PROCESS FOR PRODUCING 3-HYDROXYMETHYL-1-PROPARGYLIMIDAZOLIDINE-2, 4-DIONE

[75] Inventors: Yoo Tanabe; Masanari Murakami, both of Nishinomiya; Hitomi Yamamoto, Osaka, all of Japan

[73] Assignee: Sumotomo Chemical Company, Ltd., Osaka, Japan

[21] Appl. No.: 20,739

[22] Filed: Feb. 22, 1993

[30] Foreign Application Priority Data

Mar. 10, 1992 [JP] Japan .................................. 4-051365

[51] Int. Cl.$^5$ .......................................... C07D 233/74
[52] U.S. Cl. ................................. 548/319.1
[58] Field of Search ..................... 548/319.1

[56] References Cited

U.S. PATENT DOCUMENTS 4,176,189 11/1979 Itaya et al. ..................... 424/273 R
4,200,758 4/1980 Henrick et al. .................... 548/312

FOREIGN PATENT DOCUMENTS 285270 10/1988 European Pat. Off. .
2095675 10/1982 United Kingdom .
2118182 10/1983 United Kingdom .

OTHER PUBLICATIONS

Orazi et al, New Route for 1-Substituted Hydantions[1], *Experientia* XXI/9, Apr. 2, 1965, p. 508.

Primary Examiner—Patricia L. Morris
Attorney, Agent, or Firm—Cushman, Darby & Cushman

[57] ABSTRACT

Disclosed is a process for producing 3-hydroxymethyl-1-propargylimidazolidine-2,4-dione which comprises
(i) reacting a compound of the formula (I)

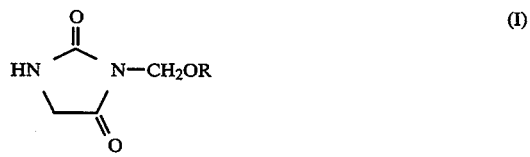

wherein R represents an alkyl, alkoxyalkyl or aralkyl group with a compound of the formula (II)

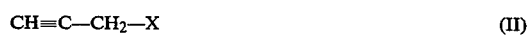

wherein X represents a leaving group in the presence of a base to give a 1-propargylimidazolidine-2,4-dione derivative of the formula (III)

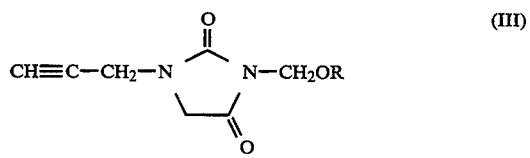

wherein R is as defined above and
(ii) hydrolyzing this derivative of the formula (III).

11 Claims, No Drawings

PROCESS FOR PRODUCING 3-HYDROXYMETHYL-1-PROPARGYLIMIDAZOLIDINE-2, 4-DIONE

The present invention relates to a process for producing 3-hydroxymethyl-1-propargylimidazolidine-2,4dione which is useful as an intermediate for the production of insecticides.

Since it is known that 3-hydroxymethyl-1-propargylimidazolidine-2,4-dione represented by the formula

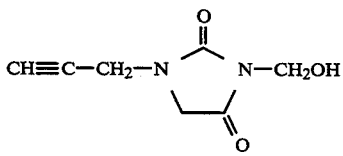

is a useful intermediate for the production of insecticidally active compounds described in U. S. Pat. No. 4,176,189, development of a commercially advantageous process for its production has been much awaited.

We made intensive investigations in an attempt to develop a process for producing 3-hydroxymethyl-1-propargylimidazolidine-2,4-dione. As a result, we found that the object can be easily achieved when the process mentioned below is used. Based on this finding, we have completed the present invention.

The present invention thus provides a process for producing 3-hydroxymethyl-1-propargylimidazolidine-2,4-dione which comprises (i) reacting a compound of the formula (I)

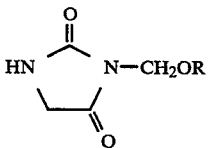 (I)

wherein R represents an alkyl, alkoxyalkyl or aralkyl group with a compound of the formula (II)

CH≡C—CH$_2$—X (II)

wherein X represents a leaving group in the presence of a base to give a 1-proparqylimidazolidine-2,4-dione derivative of the formula (III)

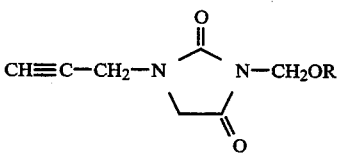 (III)

wherein R is as defined above and (ii) hydrolyzing this derivative of the formula (III).

Referring, first, to R in the above formulas (I) and (III), the alkyl group includes lower (e.g. $C_1$ to $C_4$) alkyl groups such as methyl, ethyl, etc.; the alkoxyalkyl group includes lower (e.g. $C_1$ to $C_4$) alkoxy-lower (e.g. $C_1$ to $C_4$) alkyl groups such as methoxyethyl, ethoxyethyl, etc.; and the aralkyl group includes phenyl-substituted lower (e.g. $C_1$ to $C_4$) alkyl groups such as benzyl, β-phenethyl, α-phenethyl and so on.

The leaving group X in the formula (II) includes halogen atoms such as chlorine, bromine, iodine, etc. and sulfonic acid residues of the formula —OSO$_2$R$^a$- wherein R$^a$ is a lower (e.g. $C_1$–$C_4$) alkyl group, a phenyl group, a tolyl group or the like. Examples of such sulfonic acid residue are methanesulfonic acid residue, p-toluenesulfonic acid residue, benzenesulfonic acid residue and so on.

The base which is used in the step (i) comprising reacting a compound of the formula (I) and a compound of the formula (II) includes alkali metal hydroxides such as potassium hydroxide, sodium hydroxide, etc. and alkali metal carbonates such as sodium carbonate, potassium carbonate and so on.

The reaction between the compound of the formula (I) and the compound of the formula (II) in the step (i) is generally conducted in a solvent, which may for example be selected from among ketones such as methyl isobutyl ketone, acetone, etc., ethers such as tetrahydrofuran etc., halogenated alkanes such as methylene chloride, 1,2-dichloroethane, etc., dimethylformamide and dimethyl sulfoxide.

This reaction is generally carried out at a temperature within the range of usually about −10° C. to about 50° C. for about 1 to about 24 hours. As for the amounts of the reactants, the compound of the formula (II) is used generally in an amount of about 1 to about 5 moles and the base is used generally in an amount of about 1 to about 2 moles, each per mole of the compound of the formula (I).

After completion of the reaction, 1-propargylimidazolidine-2,4-dione derivative of the formula (III) can be isolated by a conventional procedure, for example by adding water to the reaction mixture, extracting it with an organic solvent and removing the solvent under reduced pressure.

Preferably, this reaction in the step (i) is conducted in the presence of an auxiliary agent such as a phase transfer catalyst. Such an auxiliary agent is used generally in an amount of about 0.001 to about 0.2 mole per mole of the compound of the formula (I). The auxiliary agent mentioned above includes, among others, tertiary amines such as tris[2-(2-methoxyethoxy)ethyl]-amine, tris(3,6-dioxaheptyl)amine, tris(3,6-dioxaoctyl)-amine, etc., quaternary ammonium salts such as tetra-n-butylammonium bromide, benzyltriethylammonium chloride, tetra-n-butylammonium sulfate, etc., crown ethers such as 18-crown-6, dicyclohexano-18-crown-6, etc., and poly-ethylene glycols such as polyethylene glycol (PEG) 400, PEG 1540, etc. These agents can be used either singly or in combination.

The resulting 1-propargylimidazolidine-2,4-dione derivative of the formula (III), either as it is in the crude form or after isolation by chromatography or the like, is subjected to the step (ii), i.e., hydrolysis to give 3-hydroxymethyl-1-propargylimidazolidine-2,4dione.

This hydrolysis reaction in the step (ii) can be carried out by treating the 1-propargylimidazolidine2,4-dione derivative of the formula (III) in an aqueous solution of an acid, such as hydrochloric acid or sulfuric acid, at a temperature in the range of about 20 to about 100° C. for about 5 minutes to about 24 hours. The amount of said acid is preferably about 1 to about 500 moles per mole of the 1-propargylimidazolidine-2, 4-dione derivative of a formula (III). After completion of hydrolysis, 3-hydroxymethyl-1-propargylimidazolidine-2,4-dione can be isolated by a conventional procedure, for example by removing the solvent under reduced pressure or diluting the reaction mixture with water and extracting it with an organic solvent. If necessary, the product compound may be further subjected to chromatography or the like.

The compound of the formula (I) for use in the present invention can be prepared by reacting imidazolidine-2,4-dione, which is readily available, with a compound of the formula (IV)

Y—CH$_2$OR wherein R is as defined hereinbefore and Y means a leaving group in the presence of a base.

Referring to the compound of the formula (IV), the leaving group Y includes halogens such as chlorine, bromine, iodine. The base for this reaction includes alkali metal hydroxides such as potassium hydroxide, sodium hydroxide, etc. and alkali metal carbonates such as sodium carbonate, potassium carbonate and so on.

The reaction between imidazolidine-2,4-dione and a compound of the formula (IV) is generally conducted in a solvent. The solvent which can be used includes ketones such as methyl isobutyl ketone, acetone, etc., ethers such as tetrahydrofuran etc., halogenated alkanes such as methylene chloride, 1,2-dichloroethane, etc., dimethylformamide, dimethyl sulfoxide and so on.

The reaction temperature is generally in the range of about −10 to about 50° C. and the reaction time is generally about 1 to about 24 hours. Per mole of imidazolidine-2,4-dione, compound of the formula (IV) is used generally in an amount of about 0.3 to about 3 moles and said base is used generally in an amount of about 0.3 to about 3 moles.

After completion of the reaction, the compound of the formula (I) can be isolated by a conventional procedure, for example by diluting the reaction mixture with water, extracting it with an organic solvent and removing the solvent under reduced pressure.

This reaction is preferably carried out in the presence of an auxiliary agent such as a phase transfer catalyst. The auxiliary agent is used generally in an amount of about 0.001 to about 0.2 moles per mole of imidazolidine-2,4-dione- The auxiliary agent which can be used includes those mentioned for the reaction between compound (I) and compound (II) in the step (i).

As described above, the compound of the formula (III) is useful as an intermediate for preparing the 3-hydroxymethyl-1-propargylimidazolidine-2,4-dione- It is advantageous in that 3-hydroxymethyl-1-propargyl-imidazolidine-2,4-dione which is a direct intermediate for the production of the active ingredient of insecticides can be produced from the compound of the formula (III) by a simple step, hydrolysis.

The following examples are only intended to describe the present invention in further detail and should by no means be construed as defining the scope of the invention.

Example 1-1

In 8 ml of methyl isobutyl ketone were dissolved 500 mg (2.27 mmoles) of 3-benzyloxymethyl-imidazolidine-2,4-dione and 37 mg (0.115 mmoles) of tetrabutylammonium bromide followed by addition of 114 mg (2.85 mmoles) of sodium hydroxide at room temperature with stirring. Thereafter, 610 mg (4.55 mmoles) of propargyl methanesulfonate was added dropwise at room temperature with stirring and the mixture was further stirred at room temperature for 7 hours. Water was added to the reaction mixture, and the mixture was extracted with ethyl acetate. The organic layer was washed with water and saturated aqueous sodium chloride solution in that order, and dried over anhydrous sodium sulfate. The solvent was distilled off under reduced pressure and the residue was subjected to silica gel column chromatography (eluent; hexane:ethyl acetate =3:1) to give 461 mg (1.78 mmoles) of 3-benzyloxymethyl-1-propargylimidazolidine-2,4-dione.

Yield 79%

$^1$H-NMR, δ(CDCl$_3$):2:35 (1H, t, J=2 Hz), 3.90 (2H, s), 4.20 (2H, d, J=2 Hz) 4.65 (2H, s), 5.05 (2H, s), 7.20–7.45 (5H,m)

Example 1-2

To 0.55 g (2.13 mmoles) of 3-benzyloxymethyl-1-propargylimidazolidine-2,4-dione was added 25 ml (304 mmoles) of concentrated (ca. 36% w/w) hydrochloric acid and the mixture was stirred at 60° C. for 1 hour. The hydrochloric acid was distilled off under reduced pressure and the residue was subjected to silica gel column chromatography (eluent; hexane:2-propanol =3:1) to give 0.20 g (1.19 mmoles) of 3-hydroxymethyl-1-pro-pargylimidazolidine-2,4-dione.

Yield 56%

$^1$H-NMR, δ(CDCl$_3$): 2.35 (1H, t, J=2 Hz), 4.05 (2H, s), 4.25 (2H, d, J=2 Hz), 5.05 (2H, s), 5.30 (1H, s, —OH)

The following reference examples pertain to the production of the compound of the formula (I) to be used in the present invention.

Reference Example 1

In 5 ml of methyl isobutyl ketone were suspended 216 mg (3.85 mmoles) of potassium hydroxide and 73 mg (0.226 mmoles) of tris[2-(2-methoxyethoxy)ethyl]-amine followed by addition of 900 mg (8.99 mmoles) of imidazolidine-2,4-dione, and the mixture was stirred at room temperature for 10 minutes. Then, 704 mg (4.50 mmoles) of benzyloxymethyl chloride was added dropwise at 0° C. and the mixture was stirred at room temperature for 3 hours. To this reaction mixture was added water and the organic layer was separated and washed successively with water and saturated aqueous sodium chloride solution and dried over anhydrous sodium sulfate. The solvent was then distilled off under reduced pressure and the residue was subjected to silica gel chromatography (eluent: hexane:ethyl acetate =1:1) to give 687 mg (3.12 mmoles) of 3-benzyloxymethylimidazolidine-2,4-dione. Yield 70% (based on benzyloxymethyl chloride) $^1$H-NMR, δ(CDCl$_3$): 3.90 (2H, s), 4.60 (2H, s), 5.05 (2H, s), 6.00–6.20 (1H, brs, -NH), 7.20–7.45 (5H, m)

Reference Example 2

Using 73 mg (0,126 mmoles) of tetrabutyl-ammonium sulfate in lieu of 73 mg of tris[2-(2-methoxyethoxy)ethyl]amine, the procedure of Reference Example 1 was otherwise repeated to give 612 mg (2.78 mmoles) of 3-benzyloxymethylimidazolidine-2,4-dione. Yield 62% (based on benzyloxymethyl chloride)

Reference Example 3

Using 73 mg (0.226 mmole) of tetrabutylammonium bromide in lieu of 73 mg of tris[2-(2-methoxyethoxy)-ethyl]amine, the procedure of Reference Example 1 was otherwise repeated to give 556 mg (2.52 mmoles) of 3-benzyloxymethylimidazolidine-2,4-dione. Yield 56% (based on benzyloxymethyl chloride)

Reference Example 4

Using 346 mg (0.225 mmole) of polyethylene glycol 1540 in lieu of 73 mg of tris[2-(2-methoxyethoxy)ethyl]amine, the procedure of Reference Example 1 was otherwise repeated to give 562 mg (2.55 mmoles) of 3-benzyloxymethylimidazolidine-2,4-dione. Yield 57% (based on benzyloxymethyl chloride)

In accordance with the process of the present invention, 3-hydroxymethyl-1-propargylimidazolidine-2,4dione, an important intermediate for the production of insecticidally active compounds, can be easily produced. Such insecticidally active compounds can be produced from said 3-hydroxymethyl-1-propargylimidazolidine-2.4-dione by the method described in U.S. Pat. No. 4,176,189.

What is claimed is:

1. A process for producing 3-hydroxymethyl-1-propargylimidazolidine-2,4-dione which comprises:
   (i) reacting a compound of the formula (I)

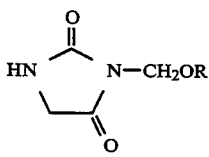
(I)

wherein R represents an alkyl, alkoxyalkyl or aralkyl group with a compound of the formula (II)

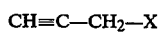  (II)

wherein X represents a halogen atom or sulfonic acid residue in the presence of a base to give a 1-propargylimidazolidine -2,4-dione derivative of the formula (III)

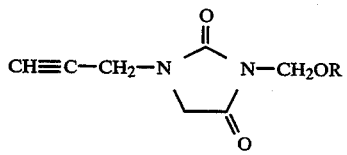
(III)

wherein R is as defined above, and
   (ii) hydrolyzing this derivative of the formula (III).

2. A process according to claim 1, wherein the hydrolysis in step (ii) is carried out in an aqueous solution of an acid.

3. A process according to claim 1, wherein the base is alkali metal hydroxides or alkali metal carbonates.

4. A process according to claim 1, wherein the reaction of step (i) is carried out in the presence of a phase transfer catalyst.

5. A process according to claim 1, wherein the compound of the formula (II) and said base are used in an amount of about 1 to about 5 moles and about 1 to about 2 moles, respectively, per mole of the compound of the formula (I).

6. A process according to claim 1, wherein the reaction in step (i) is carried out at a temperature within the range of about −10° to about 50° C. and the hydrolysis in step (ii) is carried out at a temperature within the range of about 20° to about 100° C.

7. A process for producing 3-hydroxymehtyl-1-propargylimidazolidine-2,4-dione which comprises:
   (i) reacting imidazolidine-2,4-dione with a compound of the formula (IV)

  (IV)

wherein R represents an alkyl group, an alkoxyalkyl group or an aralkyl group and Y represents a halogen atom to obtain a compound of the formula (I):

(I)

wherein R represents an alkyl, alkoxyalkyl or aralkyl group,
   (ii) reacting a compound of the formula (I) with a compound of the formula (II)

  (II)

wherein X represents a halogen atom or sulfonic acid residue in the presence of a base to give a 1-propargylimidazolidine-2,4-dione derivative of the formula (III)

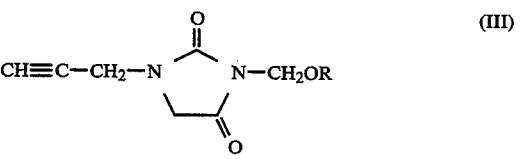
(III)

wherein R is as defined above, and
   (iii) hydrolyzing this derivative of the formula (III).

8. A process according to claim 1, wherein the halogen atom is chlorine, bromine or iodine and the sulfonic acid residue is $-OSO_2R^4$ wherein $R^4$ is $C_1$ to $C_4$ alkyl, phenyl or tolyl.

9. A process according to claim 7 wherein the halogen atom is chlorine, bromine, or iodine.

10. A process for producing 3-hydroxymethyl-1-propargylimidazolidine -2,4-dione according to claim 1, wherein R represents ($C_1$-$C_4$) alkyl, ($C_1$-$C_4$) alkoxy ($C_1$-$C_4$) alkyl, or phenyl substituted ($C_1$-$C_4$) alkyl.

11. A process for producing 3-hydroxymethyl-1-propargylimidazolidine -2,4-dione according to claim 7, wherein R represents ($C_1$-$C_4$) alkyl, ($C_1$-$C_4$) alkoxy ($C_1$-$C_4$) alkyl, or phenyl substituted ($C_1$-$C_4$) alkyl.

* * * * *